US009714969B2

(12) United States Patent
Kosturko (10) Patent No.: US 9,714,969 B2
(45) Date of Patent: Jul. 25, 2017

(54) SYSTEMS AND METHODS FOR SPECTROSCOPIC MEASUREMENT OF A CHARACTERISTIC OF BIOLOGICAL TISSUE

(71) Applicant: CAS Medical Systems, Inc., Branford, CT (US)

(72) Inventor: William Kosturko, Milford, CT (US)

(73) Assignee: CAS Medical Systems, Inc., Branford, CT (US)

( * ) Notice: Subject to any disclaimer, the term of this patent is extended or adjusted under 35 U.S.C. 154(b) by 579 days.

(21) Appl. No.: 14/041,733

(22) Filed: Sep. 30, 2013

(65) Prior Publication Data

US 2014/0100823 A1    Apr. 10, 2014

Related U.S. Application Data

(60) Provisional application No. 61/707,138, filed on Sep. 28, 2012.

(51) Int. Cl.
| | |
|---|---|
| *H03F 1/26* | (2006.01) |
| *G01R 29/26* | (2006.01) |
| *A61B 5/00* | (2006.01) |
| *A61B 5/1455* | (2006.01) |
| *G01N 21/00* | (2006.01) |

(52) U.S. Cl.
CPC ............ *G01R 29/26* (2013.01); *A61B 5/0075* (2013.01); *A61B 5/14553* (2013.01); *G01N 21/00* (2013.01); *A61B 5/7225* (2013.01); *A61B 2576/026* (2013.01)

(58) Field of Classification Search
CPC ...... G01N 21/00; G01R 29/26; A61B 5/0075; A61B 5/14553; A61B 5/7225; A61B 2576/026

USPC ........ 702/191; 356/28.5; 600/476, 323, 301, 600/309, 473
See application file for complete search history.

(56) References Cited

U.S. PATENT DOCUMENTS

| | | | | |
|---|---|---|---|---|
| 4,476,875 | A * | 10/1984 | Nilsson ............. | A61B 5/02416 356/28.5 |
| 5,760,942 | A | 6/1998 | Bryant | |
| 5,801,826 | A | 9/1998 | Williams | |
| 7,139,603 | B2 * | 11/2006 | Chance ................ | A61B 5/0073 600/473 |

(Continued)

FOREIGN PATENT DOCUMENTS

GB             760729            11/1956

OTHER PUBLICATIONS

EP search report for EP13186637.8.

*Primary Examiner* — Aditya Bhat
(74) *Attorney, Agent, or Firm* — O'Shea Getz P.C.

(57) ABSTRACT

A method and system for spectroscopic measurement of a characteristic of a biological tissue is provided. The method includes the steps of: (1) using at least one light source to emit light that penetrates the biological tissue; (2) using at least one light detector to detect light emitted by the at least one light source and passed through the biological tissue, and to convert the detected light into a detection signal, the detection signal including an unwanted noise component; and (3) using a processor to process the detection signal and to determine an adjusted peak-to-peak amplitude value that is representative of an amplitude of the detection signal adjusted for the unwanted noise component.

7 Claims, 11 Drawing Sheets

(56) References Cited

U.S. PATENT DOCUMENTS

| | | | |
|---|---|---|---|
| 8,188,433 B2 | 5/2012 | Gonopolskiy et al. | |
| 2006/0058683 A1* | 3/2006 | Chance | A61B 5/0059 600/476 |
| 2007/0135694 A1 | 6/2007 | Sato | |
| 2008/0015424 A1* | 1/2008 | Bernreuter | A61B 5/14551 600/323 |
| 2008/0255433 A1* | 10/2008 | Prough | A61B 5/0095 600/301 |
| 2008/0319285 A1* | 12/2008 | Hancock | A61B 5/0507 600/309 |
| 2015/0282716 A1* | 10/2015 | Smeltzer | G01N 33/569 600/431 |

\* cited by examiner

*FIG. 13*

SYSTEMS AND METHODS FOR SPECTROSCOPIC MEASUREMENT OF A CHARACTERISTIC OF BIOLOGICAL TISSUE

This application claims priority to U.S. Patent Appln. No. 61/707,138 filed Sep. 28, 2012.

BACKGROUND INFORMATION

Spectroscopic devices are commonly used to non-invasively measure a characteristic of biological tissue. Spectroscopic devices emit light into biological tissue and detect differences in light absorption to determine the concentration of certain constituents in the biological tissue (e.g., oxygen, hemoglobin, melanin, etc.). The performance of a spectroscopic device is dependent upon its ability to generate sufficient optical power to penetrate the biological tissue of interest and to distinguish against confounding noise (e.g., caused by background light or electrical interference within the environment). Signal-to-noise considerations favor maximizing the optical power of the light emitted into the biological tissue. However, problems can arise when spectroscopic devices output high optical power light for extended periods of time or at fast repetition rates. For example, under certain operation conditions, spectroscopic devices may become undesirably hot. To avoid such problems, spectroscopic devices may be configured to output high optical power light for only short, sequential durations of time. Such spectroscopic devices detect light signals over short, sequential durations of time. The short duration of the detected light signals can make it difficult to use aggressive filtering techniques to remove confounding noise from the detected light signals; e.g., aggressive filtering techniques may add distortion to short duration detected light signals. Aspects of the present invention are directed to systems and methods for spectroscopic measurement of a characteristic of biological tissue which involve output of light having high optical power, short duration, and/or fast repetition rate, which prevent a spectroscopic device from becoming undesirably hot, which involve filtering detected light signals to remove confounding noise, and which account for distortion added to detected light signals during filtering.

SUMMARY OF THE INVENTION

According to an aspect of the present invention, a system for spectroscopic measurement of a characteristic of a biological tissue is provided. The system includes at least one light source, at least one light detector, and a processor. The at least one light source is operable to emit light that penetrates the biological tissue. The at least one light detector is operable to detect light emitted by the at least one light source and passed through the biological tissue, and is operable to convert the detected light into a detection signal, the detection signal including an unwanted noise component. The processor is operable to receive the detection signal, and is operable to determine an adjusted peak-to-peak amplitude value that is representative of an amplitude of the detection signal adjusted for the unwanted noise component.

According to another aspect of the present invention, a method for spectroscopic measurement of a characteristic of a biological tissue is provided. The method includes the steps of: (1) using at least one light source to emit light that penetrates the biological tissue; (2) using at least one light detector to detect light emitted by the at least one light source and passed through the biological tissue, and to convert the detected light into a detection signal, the detection signal including an unwanted noise component; and (3) using a processor to process the detection signal and to determine an adjusted peak-to-peak amplitude value that is representative of an amplitude of the detection signal adjusted for the unwanted noise component.

These and other features and advantages of the present invention will become apparent in light of the drawings and detailed description of the present invention provided below.

DESCRIPTION OF THE INVENTION

Figure 1:
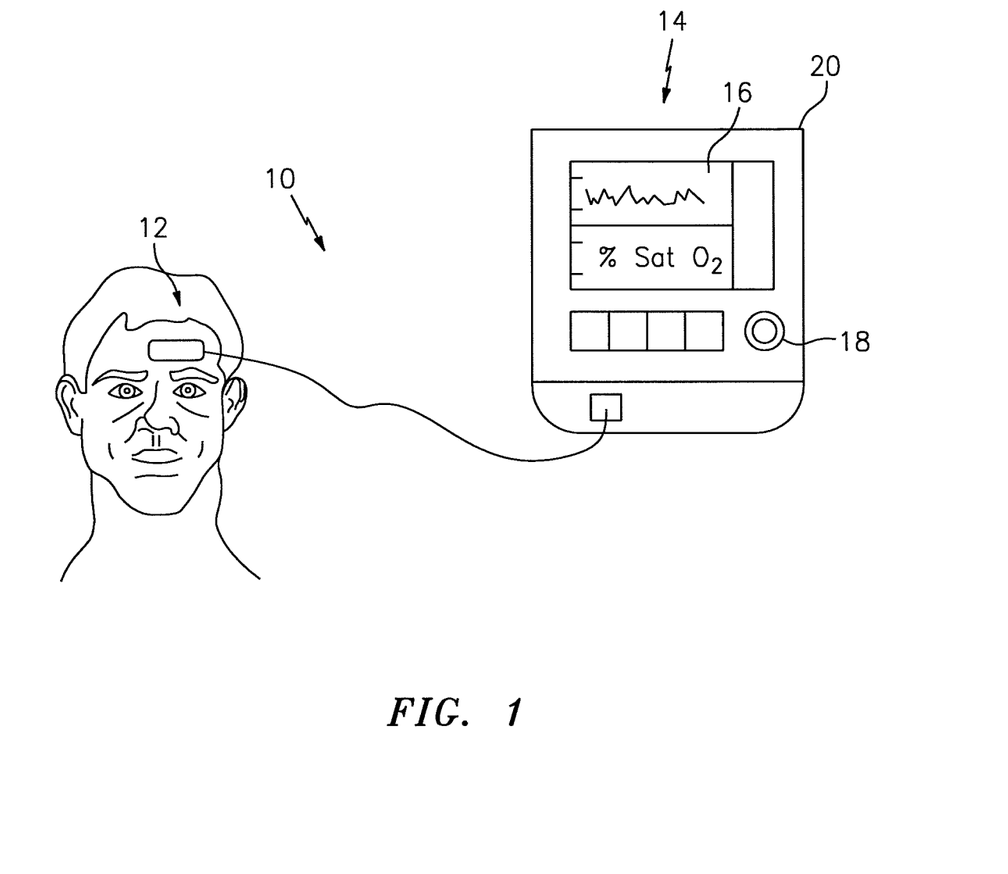
FIG. 1 is a diagrammatic illustration of a spectroscopy system embodiment.

Referring to FIG. 1, an embodiment of the present spectroscopy system 10 includes at least one sensor assembly 12 connected to a base unit 14. In FIG. 1, the sensor assembly 12 is applied to a subject. The base unit 14 includes a display 16, operator controls 18, and a processor 20 for providing signals to and/or receiving signals from the sensor assembly 12. The processor 20 is configured to selectively perform the functions necessary to operate the sensor assembly 12. For ease of description, the functionality of the processor 20 will be described herein as being implemented at least in part using hardware—specifically, a detection circuit 22, discussed in detail below. A person skilled in the art will recognize that the functionality of the processor 20 might alternatively be implemented using other hardware, software, firmware, or a combination thereof.

Figure 2:
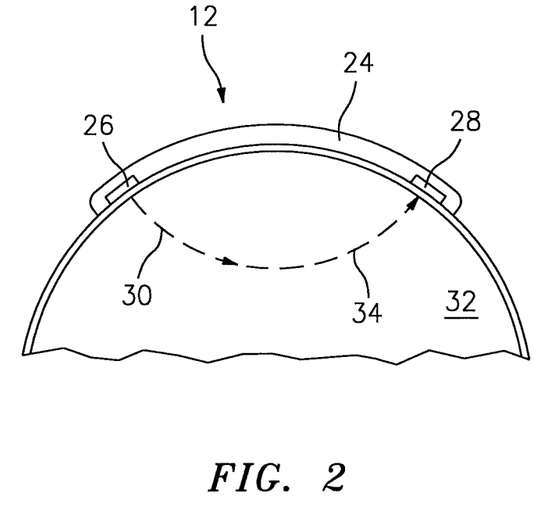
FIG. 2 is a diagrammatic illustration of a sensor assembly embodiment applied to a subject.

FIG. 2 illustrates a sensor assembly 12 embodiment applied to a subject. The sensor assembly 12 includes a pad 24, a light source 26, and a light detector 28. The light source 26 and the light detector 28 are mounted to the pad 24. The light source 26 may be any device operable to emit light; e.g., the light source 26 may be a laser, a light emitting diode (LED), or another device. The light source 26 may emit light at one or more wavelengths. The light detector 28 may be any device operable to detect light emitted by the light source 26; e.g., the light detector 28 may be a photodiode, or another device. Although the system 10 illustrated in FIG.

1 includes only one light source 26 and one light detector 28, in some embodiments the system 10 may include more than one light source 26 and/or more than one light detector 28.

Figure 3:
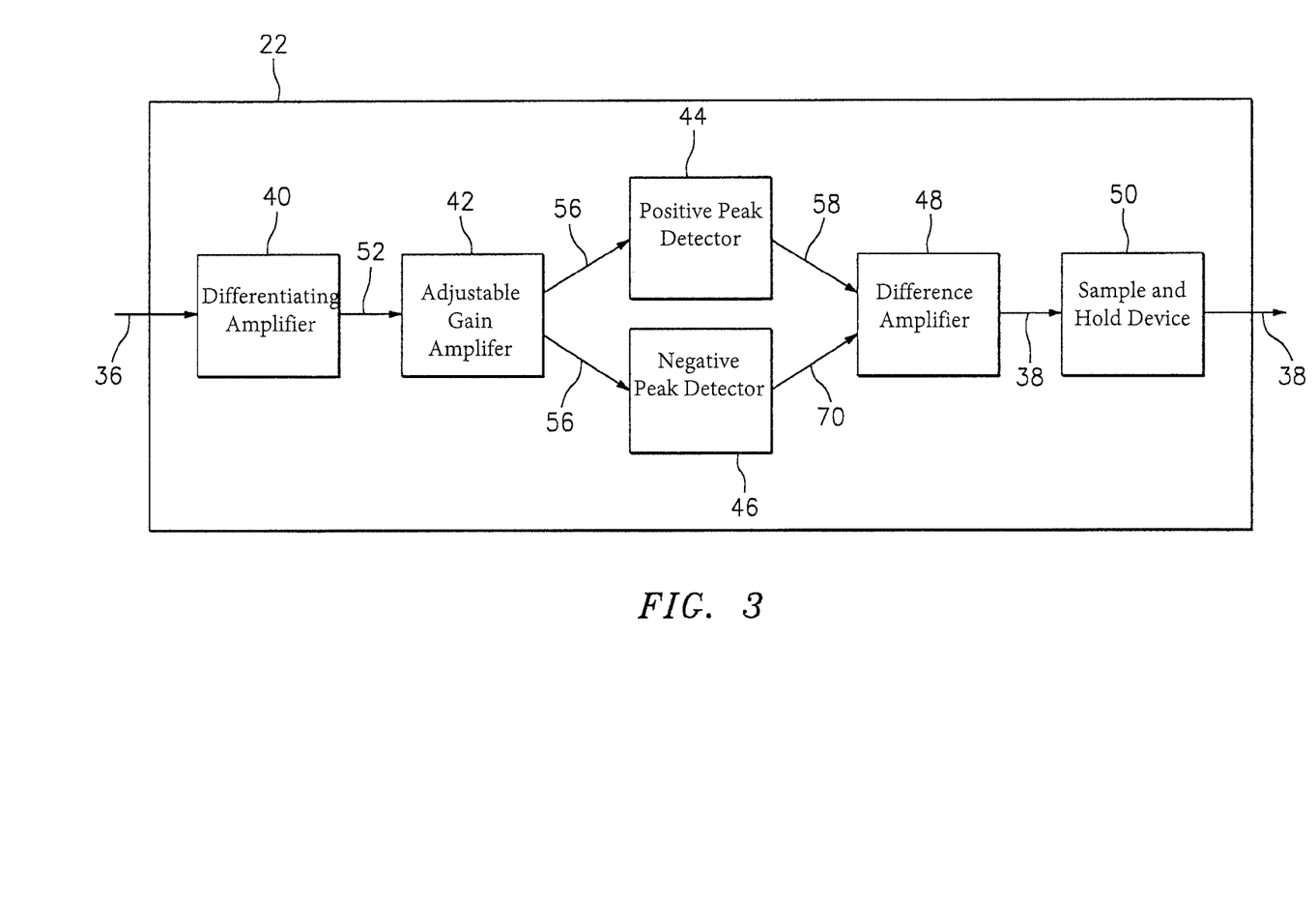
FIG. 3 is a diagrammatic illustration of a detection circuit embodiment.

Referring to FIG. 2, the sensor assembly 12 may be applied to a user so that the light source 26 emits input light 30 that penetrates a biological tissue of interest 32. In FIG. 2, the biological tissue of interest 32 is the brain. In alternative embodiments, the biological tissue of interest 32 may be tissue of the human finger, tissue of the human abdomen, or some other biological tissue. The input light 30 travels through the tissue 32 where it is attenuated, and subsequently exits the tissue as output light 34, and is detected by the light detector 28. The light detector 28 converts the detected output light 34 into a detection signal 36 (see FIG. 3). The detection signal 36 may include an unwanted noise component that results, for example, from background light detected by the light detector 28. As shown in FIG. 3, the detection signal 36 is input to the detection circuit 22. As will be discussed in detail below, the detection circuit 22 outputs an adjusted peak-to-peak amplitude value 38 that is representative of the amplitude of the detection signal 36 adjusted for an unwanted noise component that may be included in the detection signal 36. The adjusted peak-to-peak amplitude value 38 thus provides an accurate measurement of a characteristic of the biological tissue of interest 32 (e.g., oxygen concentration, hemoglobin concentration, melanin concentration, etc.).

Referring to FIGS. 3-12, an embodiment of the detection circuit 22 includes a differentiating amplifier 40, an adjustable gain amplifier 42, a positive peak detector 44, a negative peak detector 46, a difference amplifier 48, and a sample and hold device 50.

Figure 4:
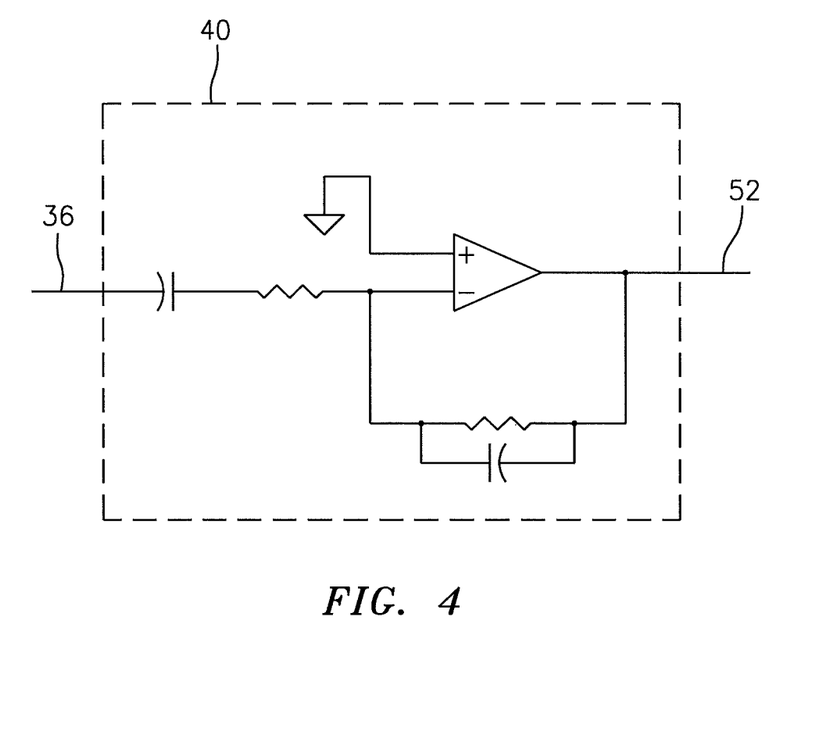
FIG. 4 is a diagrammatic illustration of a differentiating amplifier embodiment.
Figures 5, 6:
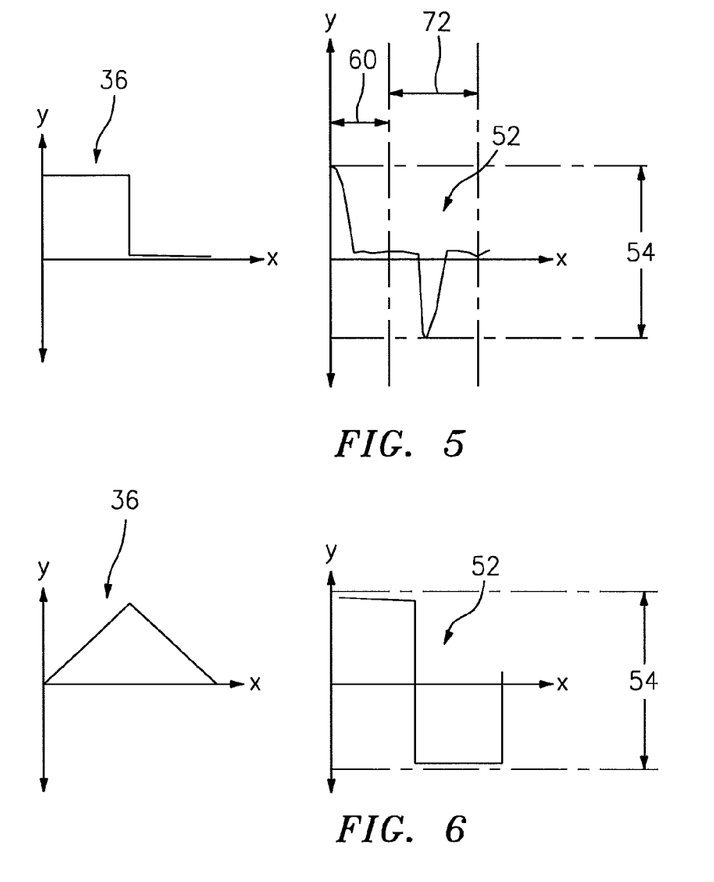
FIG. 5 is a plot showing a detection signal and its corresponding differentiated detection signal.
FIG. 6 is a plot showing a detection signal and its corresponding differentiated detection signal.
Figure 7:
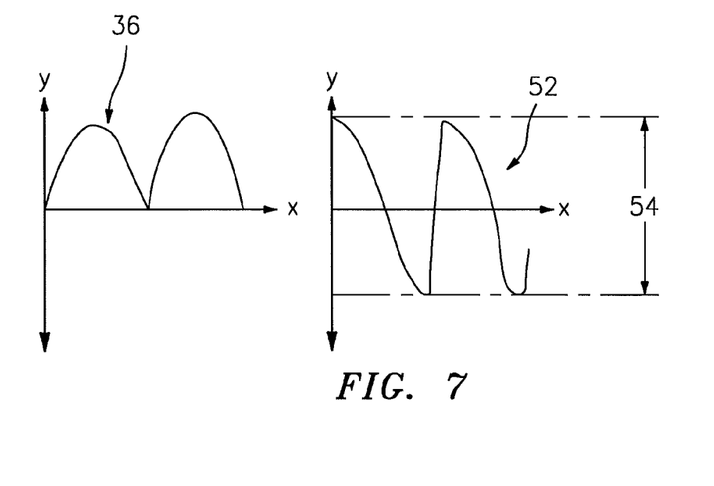
FIG. 7 is a plot showing a detection signal and its corresponding differentiated detection signal.

Referring to FIGS. 3 and 4, the differentiating amplifier 40 receives the detection signal 36 and outputs a differentiated detection signal 52. The differentiated detection signal 52 is the first derivative of the detection signal 36. Whereas the detection signal 36 is a unipolar waveform, the differentiated detection signal 52 is a bipolar waveform. The differentiating amplifier 40 functions like a high-pass filter, removing some or all of the low frequency components of the detection signal 36, which low frequency components may correspond to an unwanted noise component that may be included in the detection signal 36. FIGS. 5-7 each illustrate a plot of a detection signal 36 and its corresponding differentiated detection signal 52. In FIGS. 5-7, the x-axes represent time and the y-axes represent voltage. The differentiated detection signal 52 includes a peak-to-peak amplitude 54. FIGS. 5-7 each illustrate the peak-to-peak amplitude 54 of the respective differentiated detection signals 52. The peak-to-peak amplitude 54 of the differentiated detection signal 52 is representative of the detection signal 36, but may include an unwanted distortion component added by the differentiating amplifier 40. Other components of the detection circuit 22 (e.g., the adjustable gain amplifier 42, the positive peak detector 44, the negative peak detector 46, the difference amplifier 48, etc.) work together to determine the adjusted peak-to-peak amplitude value 38. The adjusted peak-to-peak amplitude value 38 accounts for an unwanted distortion component that may be added by the differentiating amplifier 40. Also, as indicated above, the adjusted peak-to-peak amplitude value 38 is representative of the amplitude of the detection signal 36 adjusted for an unwanted noise component that may be included in the detection signal 36. The differentiating amplifier 40 is not limited to the embodiment illustrated in FIG. 4.

Figure 8:
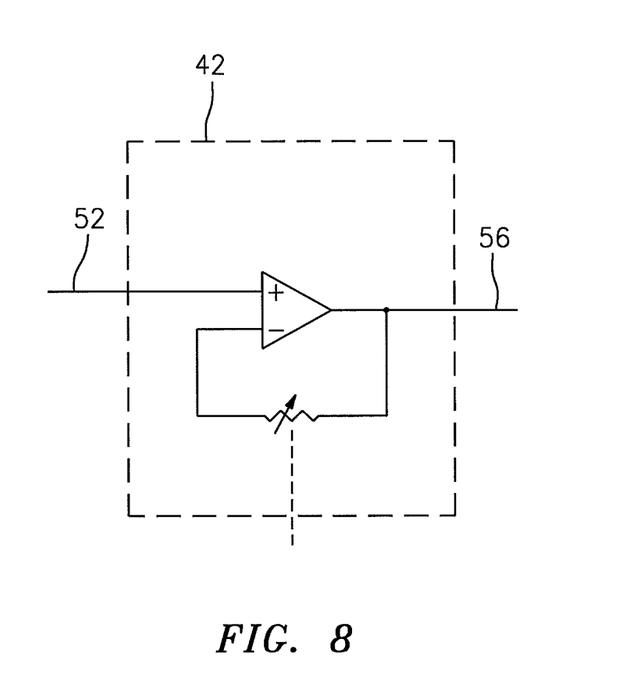
FIG. 8 is a diagrammatic illustration of an adjustable gain amplifier embodiment.

Referring to FIGS. 3 and 8, the adjustable gain amplifier 42 receives the differentiated detection signal 52 and outputs the differentiated and gain-adjusted detection signal 56. The adjustable gain amplifier 42 multiplies the differentiated detection signal 52 by a multiplication factor to produce the differentiated and gain-adjusted detection signal 56. The multiplication factor is selected to optimize the system 10 and to enable the system 10 to achieve a maximum dynamic range under most operational conditions. The adjustable gain amplifier 42 is not limited to the embodiment illustrated in FIG. 8.

Figure 9:
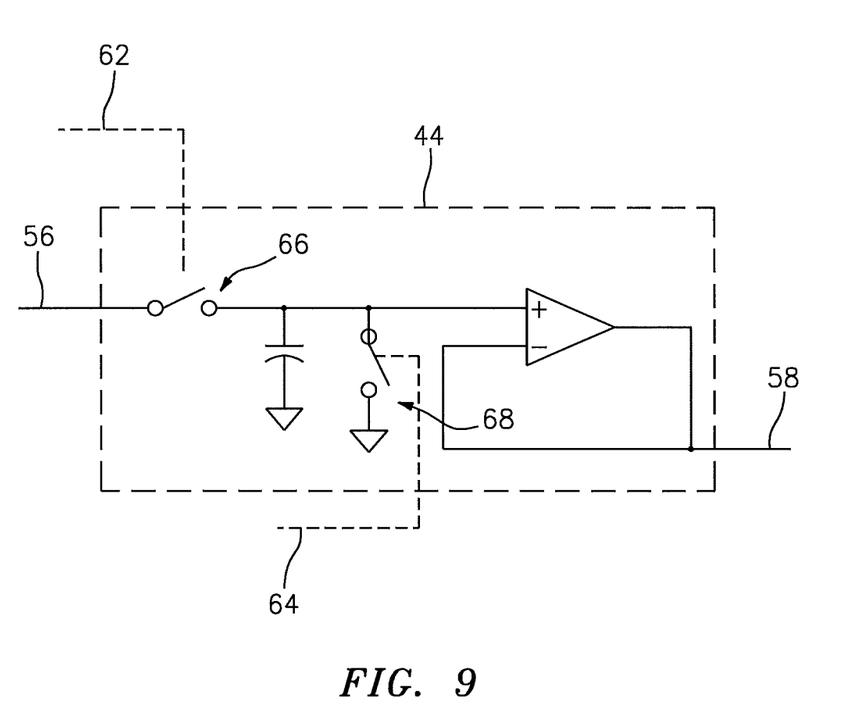
FIG. 9 is a diagrammatic illustration of a positive peak detector embodiment.

Referring to FIGS. 3 and 9, the positive peak detector 44 receives the differentiated and gain-adjusted detection signal 56. At an appropriate time period relating to a transition of the differentiated and gain-adjusted detection signal 56, the positive peak detector 44 captures, holds, and ultimately outputs the maximum value of the differentiated and gain-adjusted detection signal 56 (hereinafter referred to as the "positive peak 58" of the differentiated and gain-adjusted detection signal 56). The positive peak detector 44 may capture and hold the positive peak 58, for example, by charging a capacitor. Referring to FIG. 5, the appropriate time period for detecting the positive peak 58 is identified by reference element "60". Timing control of the positive peak detector 44 can be implemented, for example, using a microcontroller or programmable logic. In the embodiment illustrated in FIG. 9, inputs 62, 64 received from a microcontroller are operable to open and close CMOS analog switches 66, 68 of the positive peak detector 44, respectively. The positive peak detector 44 is not limited to the embodiment illustrated in FIG. 9.

Figure 10:
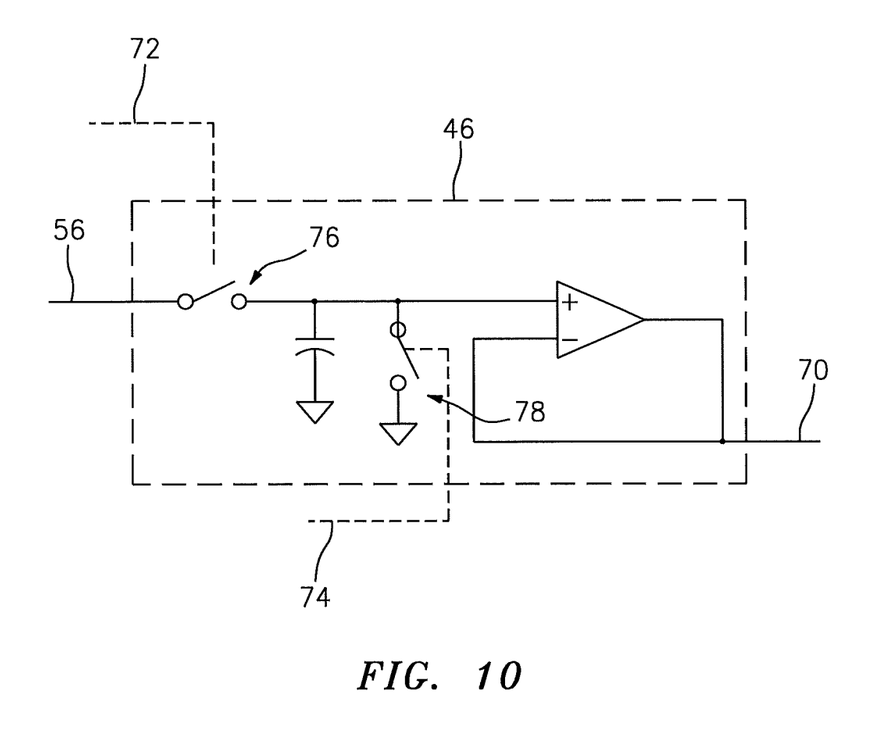
FIG. 10 is a diagrammatic illustration of a negative peak detector embodiment.

Referring to FIGS. 3 and 10, the negative peak detector 46 receives the differentiated and gain-adjusted detection signal 56. At an appropriate time period relating to a transition of the differentiated and gain-adjusted detection signal 56, the negative peak detector 46 captures, holds, and ultimately outputs the minimum value of the differentiated and gain-adjusted detection signal 56 (hereinafter referred to as the "negative peak 70" of the differentiated and gain-adjusted detection signal 56). The negative peak detector 46 may capture and hold the negative peak 70, for example, by charging a capacitor. Referring to FIG. 5, the appropriate time period for detecting the negative peak 70 is identified by reference element "72". In the embodiment illustrated in FIG. 10, inputs 72, 74 received from a microcontroller are operable to open and close CMOS analog switches 76, 78 of the negative peak detector 46, respectively. The negative peak detector 46 is not limited to the embodiment illustrated in FIG. 10.

Figure 11:
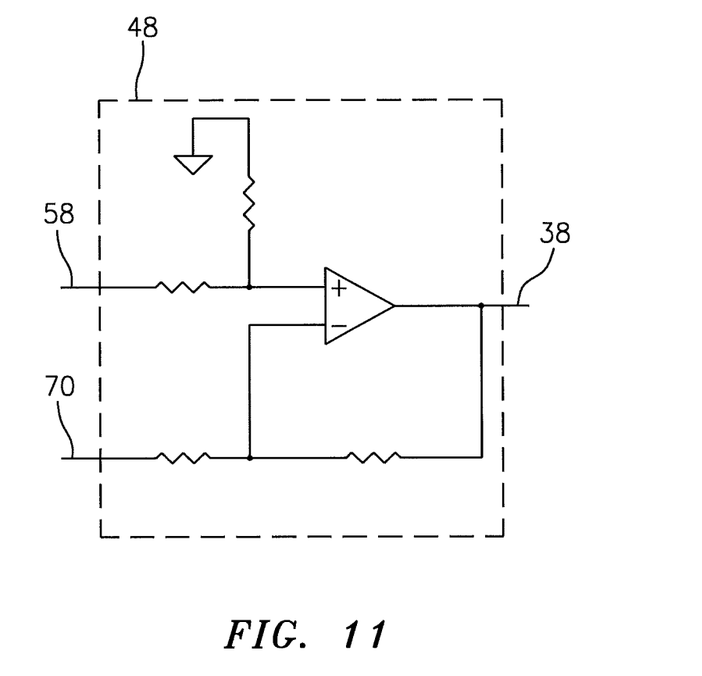
FIG. 11 is a diagrammatic illustration of a difference amplifier embodiment.

Referring to FIGS. 3 and 11, the difference amplifier 48 receives as inputs the positive peak 48 and the negative peak 70 output by the positive peak detector 44 and the negative peak detector 46, respectively. The difference amplifier 48 determines the absolute value of the sum of the positive peak 58 and the negative peak 70, and outputs this value as the adjusted peak-to-peak amplitude value 38 described above. In some instances, unwanted signal components (e.g., unwanted noise components, unwanted distortion components, etc.) may be present in the differentiated and gain-adjusted detection signal 56. Such unwanted signal components are processed by both the positive peak detector 44 and the negative peak detector 46, and thus are cancelled out when the difference amplifier 48 determines the absolute value of the sum of the positive peak 58 and the negative peak 70. The difference amplifier 48 is not limited to the embodiment illustrated in FIG. 11.

Figure 12:
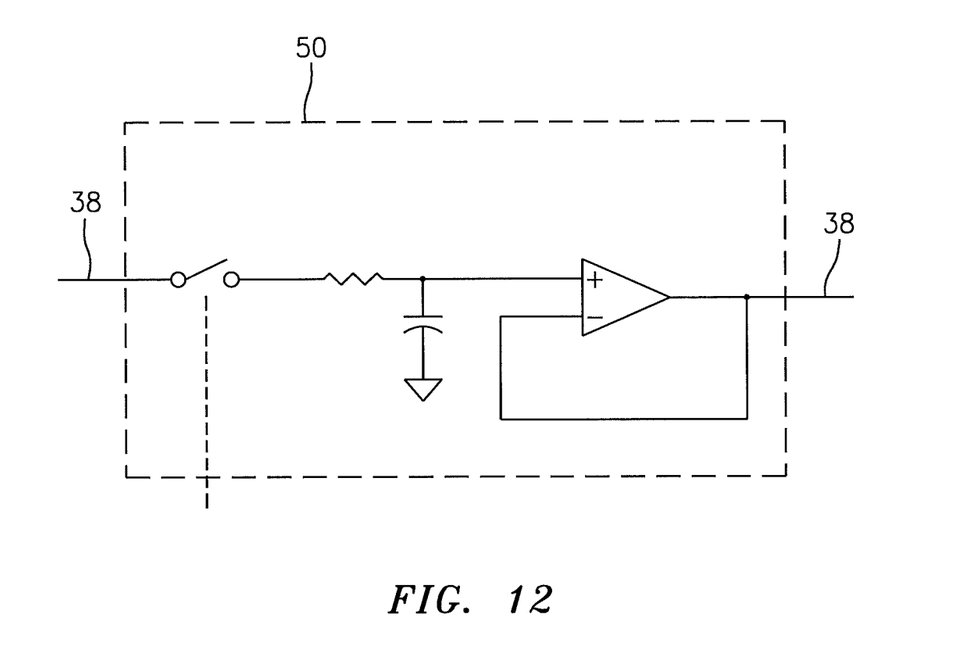
FIG. 12 is a diagrammatic illustration of a sample and hold device embodiment.

Referring to FIGS. 3 and 12, the sample and hold device 50 receives the adjusted peak-to-peak amplitude value 38 that is output by the difference amplifier 48. The sample and hold device 50 captures and holds the adjusted peak-to-peak amplitude value 38 until it can be read by the processor 20 of the system 10, at which time the sample and hold device 50 outputs the adjusted peak-to-peak amplitude value 38. The sample and hold device 50 is not limited to the embodiment illustrated in FIG. 12.

Operation

Figure 13:
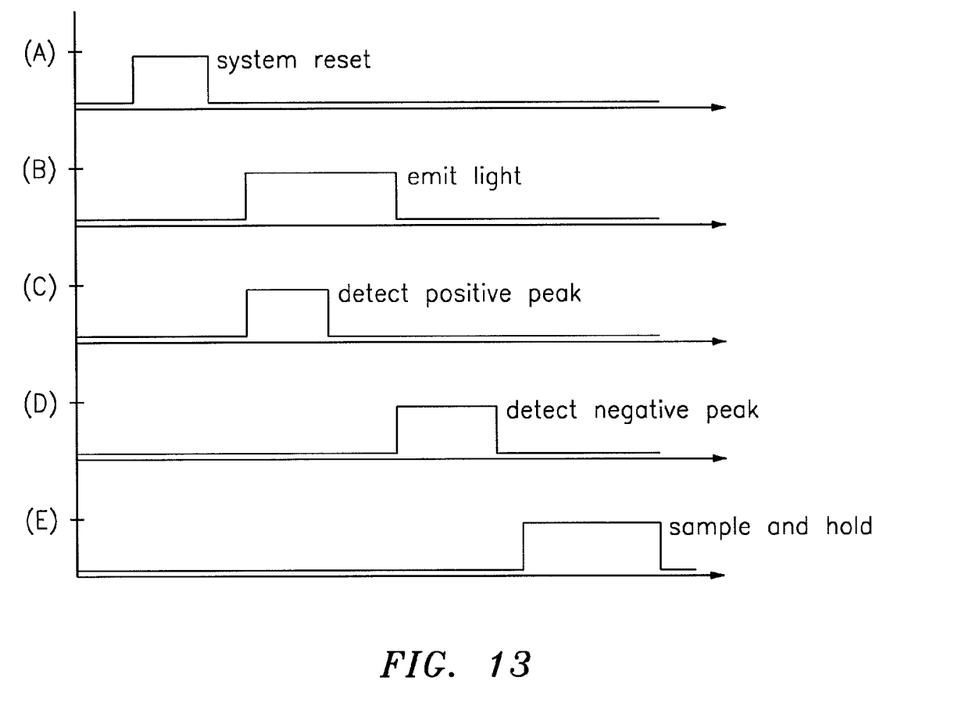
FIG. 13 is a timing diagram for the spectroscopy system.

FIG. 13 illustrates a timing diagram for the system 10 illustrated in FIGS. 1-12. In FIG. 13, steps (A) through (E) are illustrated. In step (A), the system 10 is reset; e.g., any values previously captured and held by the positive peak detector 44, the negative peak detector 46, and the sample and hold device 50 are erased or reset. In step (B), for a predetermined period of time, the light source 26 emits input light 30 that penetrates the biological tissue of interest 32. In step (C), towards the beginning of the predetermined period of time of light emission by the light source 26, the light detector 28 detects the attenuated output light 34 exiting the biological tissue of interest 32, and converts the output light 34 into a detection signal 36, and the detection circuit 22 captures and holds the positive peak 58. In step (D), towards the end of the predetermined period of time of light emission by the light source 26, the detection circuit 22 captures and holds the negative peak 70. In step (E), the sample and hold device 50 receives from the difference amplifier 48 the adjusted peak-to-peak amplitude value 38, which is representative of the absolute value of the sum of the positive peak 58 and the negative peak 70. In step (E), the sample and hold device 50 captures and holds the adjusted peak-to-peak amplitude value 38 until it can be read by the processor 20 of the system 10. Steps (A) through (E) are sequentially repeated, providing the processor 20 with a plurality of adjusted peak-to-peak amplitude values 38, each being representative of the amplitude of the detection signal 36 adjusted for an unwanted noise component that may be included in the detection signal 36.

While various embodiments of the present invention have been disclosed, it will be apparent to those of ordinary skill in the art that many more embodiments and implementations are possible within the scope of the invention. Accordingly, the present invention is not to be restricted except in light of the attached claims and their equivalents.

What is claimed is:

1. A system for spectroscopic measurement of a characteristic of a biological tissue, the system comprising:
   at least one light source operable to emit light that penetrates the biological tissue;
   at least one light detector operable to detect light emitted by the at least one light source and passed through the biological tissue, and operable to convert the detected light into a detection signal; and
   a processor operable to receive the detection signal, and operable to determine an adjusted peak-to-peak amplitude value that is representative of an amplitude of the detection signal adjusted to account for an unwanted noise component present in the detection signal,
   wherein the processor includes a detector circuit, the detector circuit comprising:
      a differentiating amplifier operable to receive the detection signal, and operable to convert the detection signal into a differentiated detection signal;
      an adjustable gain amplifier operable to receive the differentiated detection signal, and operable to convert the differentiated detection signal into a differentiated and gain-adjusted detection signal;
      a positive peak detector operable to receive the differentiated and gain-adjusted detection signal, and operable to determine a maximum value of the differentiated and gain-adjusted detection signal; and
      a negative peak detector operable to receive the differentiated and gain-adjusted detection signal, and operable to determine a minimum value of the differentiated and gain-adjusted detection signal.

2. The system of claim 1, the detector circuit comprising:
   a difference amplifier operable to determine the adjusted peak-to-peak amplitude value using the maximum value received from the positive peak detector and the minimum value received from the negative peak detector; and
   a sample and hold device operable to receive and hold the adjusted peak-to-peak amplitude value.

3. The system of claim 1, wherein the characteristic of the biological tissue is selected from the group consisting of: oxygen saturation, hemoglobin concentration, and melanin concentration.

4. The system of claim 1, wherein the processor is operable to determine the adjusted peak-to-peak amplitude value using the maximum value and the minimum value.

5. A method for spectroscopic measurement of a characteristic of a biological tissue, the method comprising the steps of:
   using at least one light source to emit light that penetrates the biological tissue;
   using at least one light detector to detect light emitted by the at least one light source and passed through the biological tissue, and to convert the detected light into a detection signal, the detection signal including an unwanted noise component; and
   using a processor to process the detection signal and to determine an adjusted peak-to-peak amplitude value that is representative of an amplitude of the detection signal adjusted for the unwanted noise component present within the detection signal,
   wherein the processor includes a detector circuit, the detector circuit comprising:
      a differentiating amplifier that receives the detection signal and converts the detection signal into a differentiated detection signal;
      an adjustable gain amplifier that receives the differentiated detection signal and converts the differentiated detection signal into a differentiated and gain-adjusted detection signal;
      a positive peak detector that receives the differentiated and gain-adjusted detection signal and determines a maximum value of the differentiated and gain-adjusted detection signal; and
      a negative peak detector that receives the differentiated and gain-adjusted detection signal and determines a minimum value of the differentiated and gain-adjusted detection signal.

6. The method of claim 5, wherein the characteristic of the biological tissue is selected from the group consisting of: oxygen saturation, hemoglobin concentration, and melanin concentration.

7. The method of claim 5, wherein the step of using the processor to process the detection signal and to determine the adjusted peak-to-peak amplitude value includes determining the adjusted peak-to-peak amplitude value using the maximum value and the minimum value.

* * * * *